US011798656B2

(12) United States Patent
Ryu (10) Patent No.: US 11,798,656 B2
(45) Date of Patent: Oct. 24, 2023

(54) COMPUTER-IMPLEMENTED METHODS AND SYSTEMS FOR IDENTIFYING A SPECIES FROM MASS SPECTRA

(71) Applicant: Nevada Research & Innovation Corporation, Reno, NV (US)

(72) Inventor: So Young Ryu, Reno, NV (US)

(73) Assignee: Nevada Research & Innovation Corporation, Reno, NV (US)

( * ) Notice: Subject to any disclaimer, the term of this patent is extended or adjusted under 35 U.S.C. 154(b) by 853 days.

(21) Appl. No.: 16/748,315

(22) Filed: Jan. 21, 2020

(65) Prior Publication Data
US 2020/0273545 A1   Aug. 27, 2020

Related U.S. Application Data

(60) Provisional application No. 62/809,285, filed on Feb. 22, 2019.

(51) Int. Cl.
*G16C 20/20* (2019.01)
*H01J 49/00* (2006.01)

(52) U.S. Cl.
CPC .......... *G16C 20/20* (2019.02); *H01J 49/0036* (2013.01)

(58) Field of Classification Search
CPC ... G16C 20/20; H01J 49/0036; G06K 9/6298; G01N 33/6896; G01N 33/57484; C12Q 1/04
See application file for complete search history.

(56) References Cited

U.S. PATENT DOCUMENTS

2006/0249667 A1* 11/2006 Goldberg ............ G06K 9/6298
                                                            250/281
2006/0269974 A1* 11/2006 Dwek ............... G01N 33/57484
                                                            435/23
(Continued)

FOREIGN PATENT DOCUMENTS

EP   1720114 A1 * 11/2006 ........... G06K 9/6298
FR   3078166 A1 *  8/2019 ......... G01N 33/4833
(Continued)

OTHER PUBLICATIONS

Fondrie, W. E., et al., "Pathogen Identification Direct From Polymicrobial Specimens Using Membrane Glycolipids", Scientific Reports 8:15857, 2018, 11 pages.
(Continued)

*Primary Examiner* — Michael J Dalbo
*Assistant Examiner* — Kaleria Knox
(74) *Attorney, Agent, or Firm* — Saul Ewing LLP; Kathryn Doyle (57) ABSTRACT

One aspect of the invention provides a computer-implemented method of identifying a species from mass spectra. The computer-implemented method includes: loading a data set including a species and associated mass spectra into memory on a computer; for each of the associated mass spectra, pre-processing to identify ranks of intensities of an in-bin peak across bins defining ranges of mass-to-charge ratio; and training a species binary classifier for each of a plurality of species using at least the ranks of intensities. Another aspect of the invention provides a system for identifying a species from mass spectra. The system includes: a processor; and computer-readable memory containing instructions to: implement an interface programmed to receive mass spectra; store the mass spectra in the
(Continued)

computer-readable memory; and invoke execution of any of the methods described herein on the processor.

11 Claims, 6 Drawing Sheets

(56) References Cited

U.S. PATENT DOCUMENTS

| | | | | |
|---|---|---|---|---|
| 2012/0197535 A1* | 8/2012 | Goodlett | ............... | C12Q 1/04 |
| | | | | 702/19 |
| 2015/0340216 A1* | 11/2015 | Kwiecien | ........... | G06K 9/00543 |
| | | | | 250/282 |
| 2020/0271672 A1* | 8/2020 | Cicchetti | ............ | G01N 33/6896 |
| 2020/0317620 A1* | 10/2020 | Puigserver | ............. | A61K 31/40 |

FOREIGN PATENT DOCUMENTS

| | | | | |
|---|---|---|---|---|
| WO | WO-2008110006 A1 * | 9/2008 | .............. | A61P 35/00 |
| WO | WO-2014071082 A2 * | 5/2014 | ........... | C12Q 1/6886 |

OTHER PUBLICATIONS

Yang, Y., et al., "Bacterial Whole Cell Typing by Mass Spectra Pattern Matching with Bootstrapping Assessment", Anal Chem. 89(22), Nov. 21, 2017, Abstract.

* cited by examiner

COMPUTER-IMPLEMENTED METHODS AND SYSTEMS FOR IDENTIFYING A SPECIES FROM MASS SPECTRA

CROSS-REFERENCE TO RELATED APPLICATION

This application claims the benefit of priority under 35 U.S.C. § 119(e) to U.S. Provisional Patent Application Ser. No. 62/809,285, filed Feb. 22, 2019. The entire content of this application is hereby incorporated by reference herein.

STATEMENT REGARDING FEDERALLY SPONSORED RESEARCH OR DEVELOPMENT

This invention was made with government support under Grant No. GM103440 awarded by the National Institutes of Health National Institute of General Medical Sciences. The government has certain rights in the invention.

BACKGROUND OF THE INVENTION

Despite public health efforts to combat antimicrobial resistance, challenges of emerging and re-emerging infections related to antimicrobial resistance remain.

SUMMARY OF THE INVENTION

One aspect of the invention provides a computer-implemented method of identifying a species from mass spectra. The computer-implemented method includes: loading a data set including a species and associated mass spectra into memory on a computer; for each of the associated mass spectra, pre-processing to identify ranks of intensities of an in-bin peak across bins defining ranges of mass-to-charge ratio; and training a species binary classifier for each of a plurality of species using at least the ranks of intensities.

This aspect of the invention can have a variety of embodiments. The computer-implemented can further include introducing decoy members into the data set. The decoy members can include shuffled ranks of intensities.

The data set can further include a phenotype for each member and the computer-implemented method can further include training a phenotype binary classifier for each of a plurality of phenotypes.

The mass spectra can have been generated using negative ion MALDI-TOF-MS analysis.

The intensities can be relative intensities.

The species can be bacterial species. The species can be selected from the group consisting of: mouse, primate, human, mammal, and animal.

The mass spectra can be glycolipid mass spectra. The mass spectra can be selected from the group consisting of: protein/peptide mass spectra and metabolite mass spectra.

Another aspect of the invention provides a computer-implemented method of identifying a species from mass spectra. The computer-implemented method includes: loading a data set including mass spectra into memory on a computer; pre-processing the mass spectra to identify at least ranks of intensities of an in-bin peak across bins defining ranges of mass-to-charge ratio; and applying the species binary classifiers created using any of the methods described herein against the ranks of intensities to identify one or more species based on a single mass spectrum.

This aspect of the invention can have a variety of embodiments. The applying step can identify a plurality of species for the single mass spectrum.

Another aspect of the invention provides a computer-implemented method of identifying a species and phenotype from mass spectra. The computer-implemented method includes: loading a data set including mass spectra into memory on a computer; pre-processing the mass spectra to identify at least ranks of intensities across bins defining ranges of mass-to-charge ratio; applying the species binary classifiers created using any of the methods described herein against at least the ranks of intensities to identify one or more species; and calculating a False-Discovery Rate (FDR) for the one or more species using decoy members; and if the FDR is less than a pre-defined threshold, applying the phenotype binary classifiers created using any of the methods described herein against at least the ranks of intensities to identify one or more phenotypes.

Another aspect of the invention provides a system for identifying a species from mass spectra. The system includes: a processor; and computer-readable memory containing instructions to: implement an interface programmed to receive mass spectra; store the mass spectra in the computer-readable memory; and invoke execution of any of the methods described herein on the processor.

BRIEF DESCRIPTION OF THE DRAWINGS

For a fuller understanding of the nature and desired objects of the present invention, reference is made to the following detailed description taken in conjunction with the accompanying drawing figures wherein like reference characters denote corresponding parts throughout the several views.

DEFINITIONS

The instant invention is most clearly understood with reference to the following definitions.

As used herein, the singular form "a," "an," and "the" include plural references unless the context clearly dictates otherwise.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

As used in the specification and claims, the terms "comprises," "comprising," "containing," "having," and the like can have the meaning ascribed to them in U.S. patent law and can mean "includes," "including," and the like.

Unless specifically stated or obvious from context, the term "or," as used herein, is understood to be inclusive.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise).

DETAILED DESCRIPTION OF THE INVENTION

To better treat infected patients and to effectively control the spread of infectious diseases, it is essential to develop accurate, affordable, and timely diagnostic tools. Profiling the Gram-negative glycolipid lipid A (and other bacterial membrane glycolipids from Gram-positive bacteria) by matrix-assisted laser desorption/ionization time-of-flight mass spectrometry (MALDI-TOF MS) is a candidate for such a rapid and low-cost diagnostic tool. Mass spectra generated from this technology contain information to identify and characterize bacteria. Not requiring biological culture, it is much faster and cheaper than currently used pathogen detection methods (e.g., morphological/biochemical method) and the protein-based MALDI-TOFMS approach.

Although described primarily in the context of bacterial glycolipids, the invention can be applied to protein/peptide mass spectra and metabolite mass spectra as well as other species beyond bacteria such as mice, humans, and other mammals and animals.

Bioinformatics tools exist that analyze MALDI-TOFMS protein-based mass spectra. For example, the MALDI BIOTYPER® mass spectrometer from Bruker Daltonics and Spectral Archive and Microbial Identification System (SARAMICS) from bioMérieux work well enough to be used in hospital clinical laboratories. Recognizing that these tools cannot differentiate closely related bacterial species (e.g., *Bacillus cereus* group), Yang 2017 proposed new measures of spectral similarity and a statistical assessment of such identifications. However, these tools are developed for information rich protein-based MALDI-TOF MS data, not the more sparse mass spectra produced by bacterial glycolipids like lipid A. To fully utilize glycolipid mass spectra for bacterial identification, it is essential to develop bioinformatics tools specific to glycolipid mass spectra like those produced by Lipid A.

Constructing meaningful theoretical Lipid A mass spectra with reasonable complexity is very challenging. A Cartesian product algorithm based on membrane glycolipid structure can in theory produce >2 billion molecular masses for a Lipid A scaffold. However, Applicant observes far fewer meaningful masses representing unique structures in real Lipid A mass spectra.

Embodiments of the invention provide a Lipid A Spectral Library (LASL) approach that utilizes mass spectra generated by known lipid A structures and related glycolipids from Gram-positive bacteria. The approach does not require theoretical mass spectra. Because the algorithm is based on acquired data, embodiments of the algorithm can reflect the stochastic nature of bacterial glycolipid ions.

Embodiments of the invention utilize a model-based spectral library approach for matching glycolipid mass spectra that referred to as Lipid A Spectral Library (LASL). Different from previously proposed spectral library approaches, LASL contains bacteria identification models instead of mass spectra or representative mass spectra. The machine-learning model can select key ions in glycolipid mass spectra during its training runs. Thus, it can work better in identifying glycolipid mass spectra than algorithms designed for protein mass spectra. LASL searches against candidate bacteria identification models instead of all mass spectra in a spectral library; thus, the search time is much faster than approaches that use all mass spectra in a spectral library. By using a model-based approach, LASL is complex enough to capture the apparently stochastic nature of glycolipid mass spectra than using only one representative mass spectrum per bacteria.

Training Binary Classifiers

Figure 1:
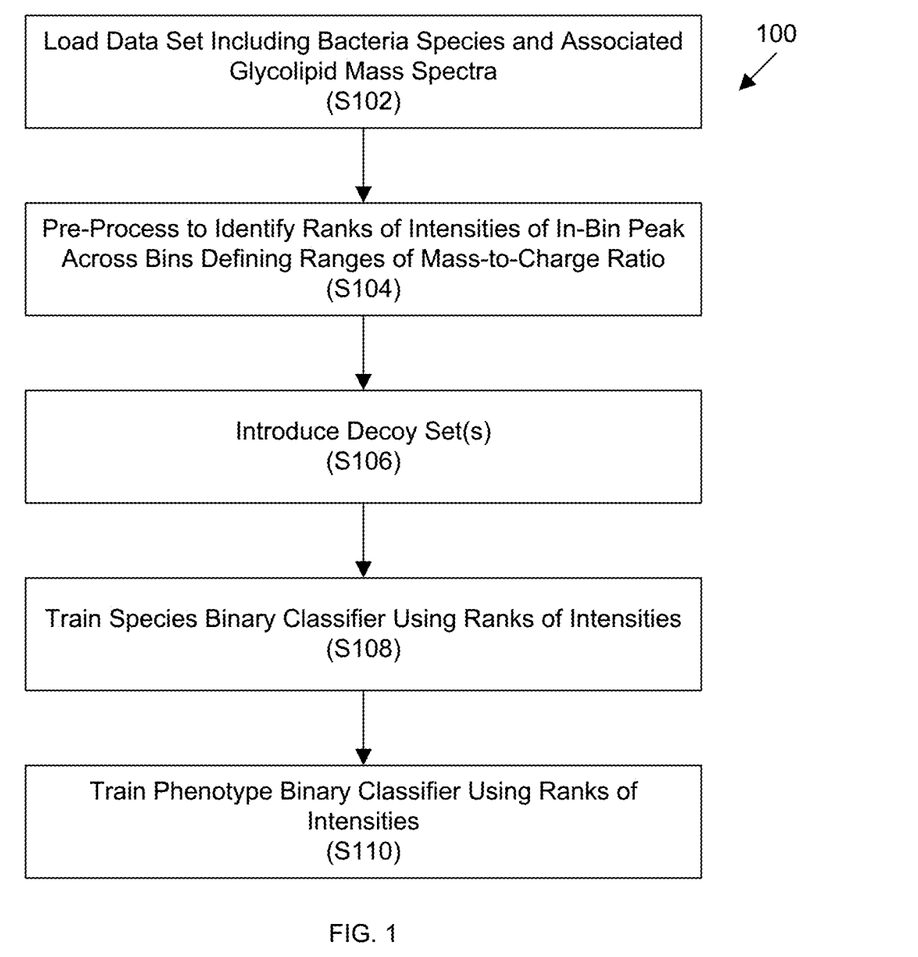
FIG. 1 depicts a method of training a binary classifier algorithm according to an embodiment of the invention.

Referring now to FIG. 1, one embodiment of the invention provides a method 100.

In step S102, a data set is loaded into memory on a computer. The data set can include a bacteria species (e.g., a taxonomic classification previously identified through other techniques) and associated glycolipid mass spectra. The mass spectra can be generated using any mass spectrometry (MS) technique including, but not limited to, Time-Of-Flight (TOF), Matrix Assisted Laser Desorption/Ionization (MALDI) TOF, and the like. An exemplary graph of mass spectra is provided in FIG. 2.

In step S104, each of the glycolipid mass spectra is pre-processed to identify ranks of intensities across bins defining ranges of mass-to-charge ratio. Bins can have equal widths (e.g., 1 Da, 10 Da, 1 m/z, 10, m/z, and the like) or unequal widths (e.g., 50-75 m/z and 75-125 m/z). Preferably, the bin widths are consistent across spectra processed under the methods described herein even if the unequal within a particular spectra to apply the same binning to all training data sets and unclassified data sets. In some embodiments, the bins overlap (e.g., 50-100 m/z, 75-125 m/z, and the like).

Figure 2:
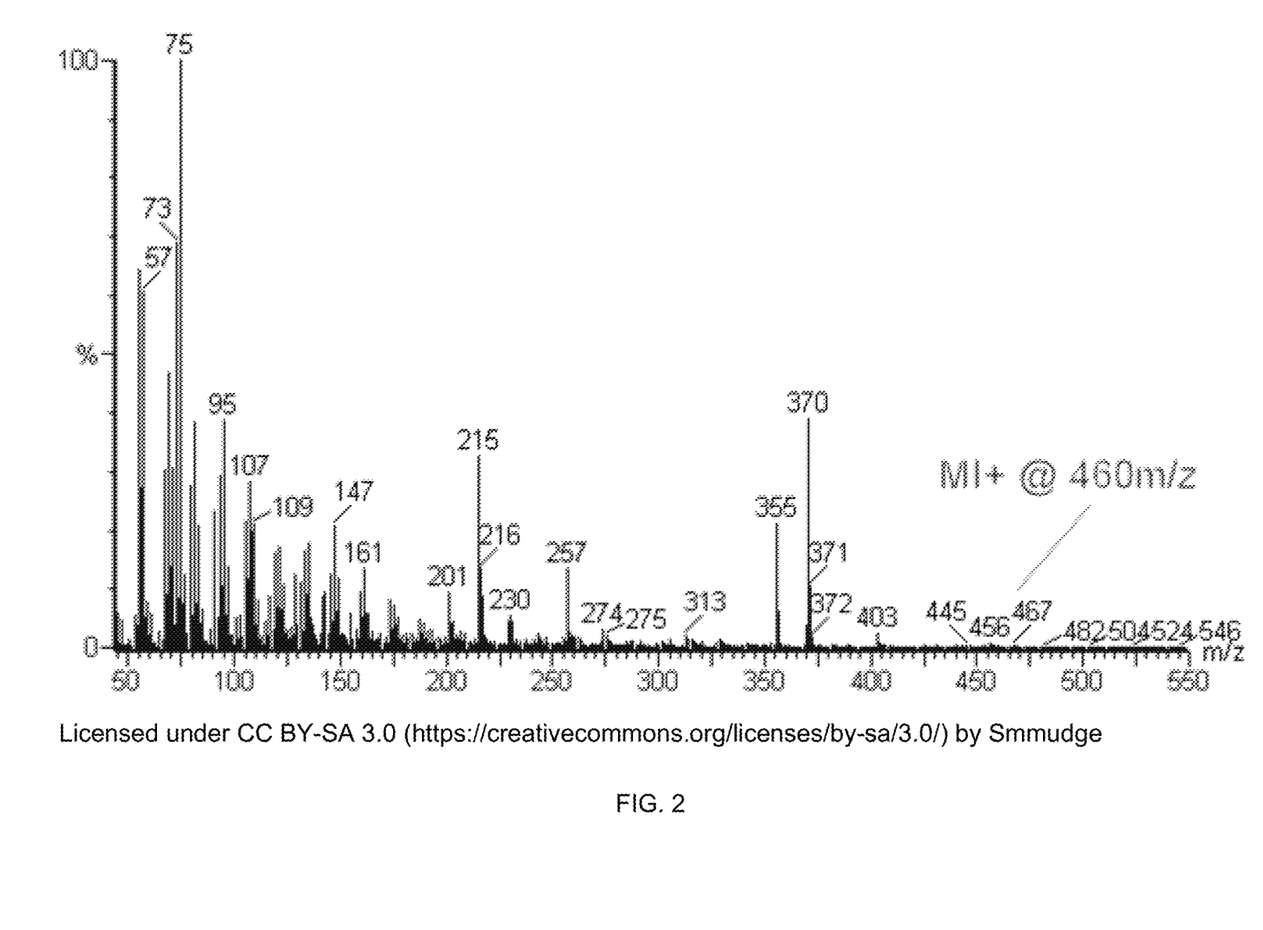
FIG. 2 depicts an exemplary mass spectrum according to an embodiment of the invention.

Using FIG. 2 as an example with 50 m/z bin width would yield the following peak values.

TABLE 1

Example bins and peak values for mass spectra depicted in FIG. 2

| Bin (m/z) | Approximate Peak Value | Rank |
|---|---|---|
| 50-100 | 100% (75 m/z) | 1 |
| 100-150 | 30% (107 m/z) | 3 |
| 150-200 | 15% (161 m/z) | 5 |
| 200-250 | 30% (215 m/z) | 3 |
| 250-300 | 12% (257 m/z) | 6 |
| 300-350 | 3% (313 m/z) | 7 |
| 350-400 | 40% (370 m/z) | 2 |
| 400-450 | 2% (403 m/z) | 8 |
| 450-500 | 1% (456 m/z) | 9 |
| 500-550 | 1% (546 m/z) | 9 |

In step S106, one or more decoy sets can be introduced. For example, decoy mass spectra can be created by extracting K (e.g., 50) random peaks in 5-10 spectra from different species and shuffling their intensities and m/z values.

In step S108, a binary classifier is trained for each of a plurality of bacteria species using at least the ranks of intensities.

In step S110, a binary classifier is trained for each of a plurality of bacteria phenotypes using at least the ranks of intensities.

A variety of binary classifiers could be used including Random Forest, stochastic gradient descent, support vector machine (using linear or non-linear kernels), and the like.

Application of Binary Classifiers

Figure 3:
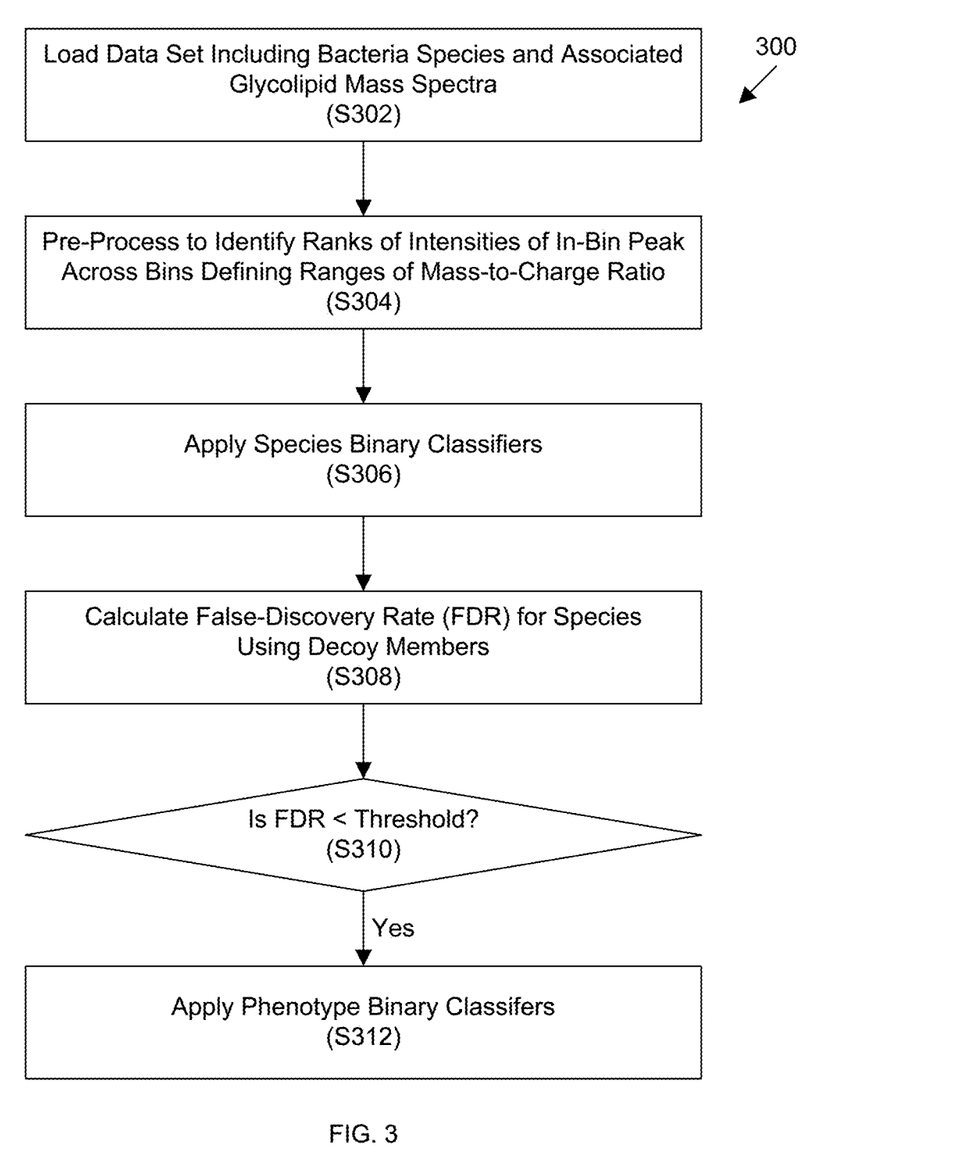
FIG. 3 depicts a method of identifying a bacteria species and/or phenotype from mass spectra according to an embodiment of the invention.

Referring now to FIG. 3, another embodiment of the invention provides a method 300.

In step S302, a data set is loaded into memory on a computer. The data set can include at least one glycolipid mass spectrum for an unknown sample. The data set can be obtained in the same manner or different manners as the data set loaded in step S102.

In step S304, each of the glycolipid mass spectra is pre-processed to identify ranks of intensities across bins defining ranges of mass-to-charge ratio. This can be performed in the same manner as in step S104.

In step S306, a previously trained species binary classifier (e.g., from step S108) can be applied against at least the ranks of intensities.

In step S308, a false-discovery rate (FDR) can be calculated for the identified species, e.g., using Equation (1).

In step S310, the FDR can be compared to a threshold. The threshold can be pre-defined, user-defined, or dynamic. In some embodiments, the threshold is about 0.01. If the FDR is less than the threshold, the method will continue. Otherwise, the method can terminate.

In step S312, a previously trained species binary classifier (e.g., from step S110) can be applied against at least the ranks of intensities.

Exemplary Implementation

Figure 4:
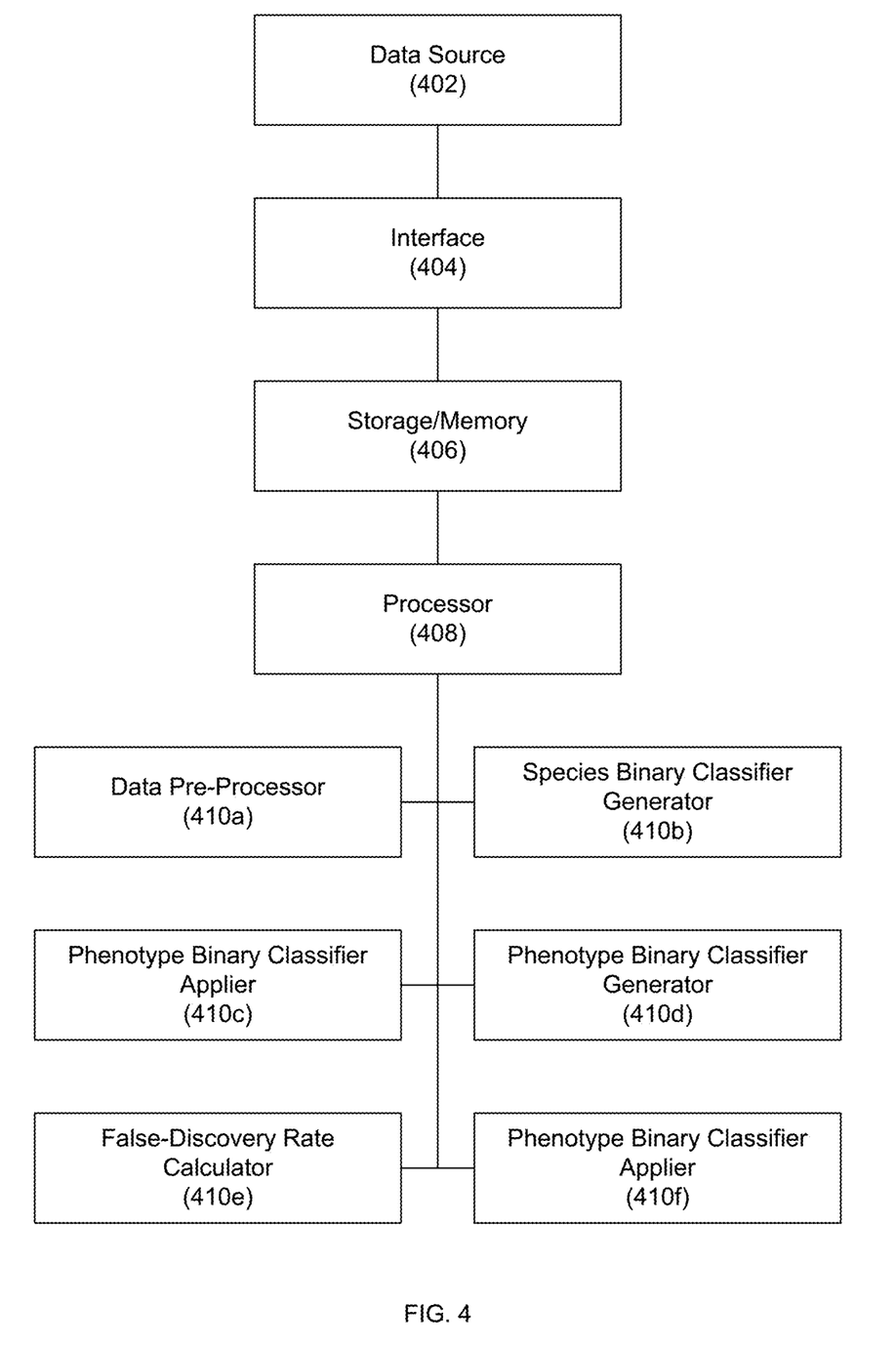
FIG. 4 depicts a computer system through which provisioned data can be interfaced, stored, and processed to identify bacteria species and/or phenotype according to an embodiment of the invention.

Referring now to FIG. 4, another embodiment of the invention provides a system 400 for implementing the methods described herein.

An interface 404 can support communication with a data source 402, which can be an internal or an external source. For example, interface 404 can be a Web page or other internet technology that allow users to upload mass spectra. The interface 404 can verify compliance with various input requirements. The interface 404 can also relay the information to storage/memory 406 and/or processor 408. For example, the interface 404 can invoke one or more processes for execution by the processor 408.

Processor 408 can load and execute one or more functions, methods, modules, objects or other computing structures to implement the methods described herein. For example, data pre-processing, species binary classifier generation, phenotype binary classifier generation, species binary classifier application, false-discovery rate calculation, and phenotype binary classifier application can be each implemented by a separate function/method/module 410a, 410b, 410c, 410d, 410e, and 410f, respectively. Such separate functions/methods/modules 410a, 410b, 410c, 410d, 410e, 410f can be invoked by an overarching function/method/module that can pass the result of a previous function/method/module to the next function/method/module, e.g., by reference to the resulting data.

Working Example

Methods

Data

Applicant used the glycolipid mass spectral dataset published by Leung 2017 that contained 906 mass spectra from various strains of six microbial species. Applicant considers these 906 glycolipid mass spectra as a main dataset. These mass spectra were generated by negative ion MALDI-TOF-MS analysis of bacterial glycolipid extracts from isolates grown in liquid culture. The dataset included 404 mass spectra of *Acinetobacter Baumannii* aa(AB), 79 from *Enterobacter Cloacae* (EC), 55 from *Enterococcus Faecalis* (EF), 207 from *Klebsiella Pneumoniae* (KP), 78 from *Pseudomonas Aeruginosa* (PA), and 83 from *Staphylococcus Aureus* (SA). There were two phenotypes available in the dataset: colistin-susceptible (cs) and colistin-resistance (cr). Applicant further denoted colistin-susceptible *Acinetobacter Baumannii* and colistin-resistance *Acinetobacter Baumannii* as ABcs and ABcr, respectively. Similarity, Applicant denoted colistin-susceptible *Klebsiella Pneumoniae* and colistinresistance *Klebsiella Pneumoniae* as KPcs and KPcr, respectively. Besides this main dataset, Applicant used a supplementary dataset of five Lipid A mass spectra generated from the following bacteria: *Burkholderia Pseudomallie, Clostridium Difficile, Legionella Bozermannii, Salmonella Typhimurium*, and *Yersinia Pseudotuberculosis*.

All mass spectra were converted to mzXML format using msconvert (v3.0.9393 ProteoWizard), then processed using the MALDIquant (v1.16.2) and MALDIquantForeign (v0.10) R packages described in Gibb 2012. Specifically, the mass spectra were square root-transformed, and smoothed using a Savitzky-Golay filter as described in Savitzky 1964. Then, the baselines of mass spectra were corrected using the Statistics-sensitive Non-linear Iterative Peak-clipping (SNIP) algorithm described in Ryan 1988, and peak intensities in mass spectra were normalized by their total ion current. The top K peaks were selected for the further analysis where K=50. Then, Applicant binned peaks by their mass-to-charge ratios with their bin sizes of 1 Da. The highest peak in each bin was selected. Their masses, (normalized) intensities, and ranks of intensities (across bins) were recorded.

Applicant created decoy mass spectra, which did not belong to any species. Only a training set from the main dataset was used for decoy spectra construction. For bacterial identification, two sets of decoy spectra were constructed. One set was used to train the model (N=1,500) and another was used to test the model performance and measure false discovery rates (N=10,000). Decoy mass spectra were created by extracting K random peaks in 5-10 spectra from different species and shuffling their intensities and m/z values where K=50. For the same purpose, Applicant also constructed two sets of decoy mass spectra for AR phenotype identification and other two sets for KP phenotype identification.

Model-Based Spectral Library

The main dataset was divided into test and train sets in a ratio of 2:1. For each set, Applicant added decoy mass spectra, which did not belong to any species. Specifically, Applicant added 1,500 mass spectra in the training set and 10,000 in the testing set. Adding decoy mass spectra in the training set improved the model performance to identify correct species with higher confidence. Decoy mass spectra in the testing set did not overlap with ones in the training set, but were used to estimate p-values and false discovery rates.

Mass spectra in the training set were used to construct a model-based spectral library. Applicant built bacteria/phenotype identification models using eXtreme Gradient Boosting (XGboost) with a logistic regression (binary classification) option as described in Chen 2016. One model was built for each microbial species. Applicant treated mass spectra from bacteria of interest as positive cases and mass spectra from other species and decoy mass spectra as negative cases.

A total of six bacterial identification models were constructed. Similarly, two phenotype models also were built for AB and two other phenotype models were built for KP.

To select the best tuning parameters for bacteria/phenotype models, Applicant used a 5-fold cross-validation and a grid search. The parameters considered were: the number of maximum iterations, η, which controlled the learning rate; γ, which controlled the regularization, the maximum depth of the tree; and the minimum sum of instance weight needed in a child.

Noting the imbalance between positive and negative cases in the dataset, Applicant set scale of positive weight as $$\Sigma \frac{\text{negative cases}}{\text{positive cases}}.$$

For example, for AB, the scale of positive weight was $$6.81 = \frac{332 + 1500}{269}$$

because there were 269 mass spectra from AB, 332 mass spectra from non-AB species, and 1,500 decoy mass spectra in the train set. In addition, Applicant set the maximum delta step for each leaf output as 1.

Bacteria/Phenotype Identification

Figure 5:
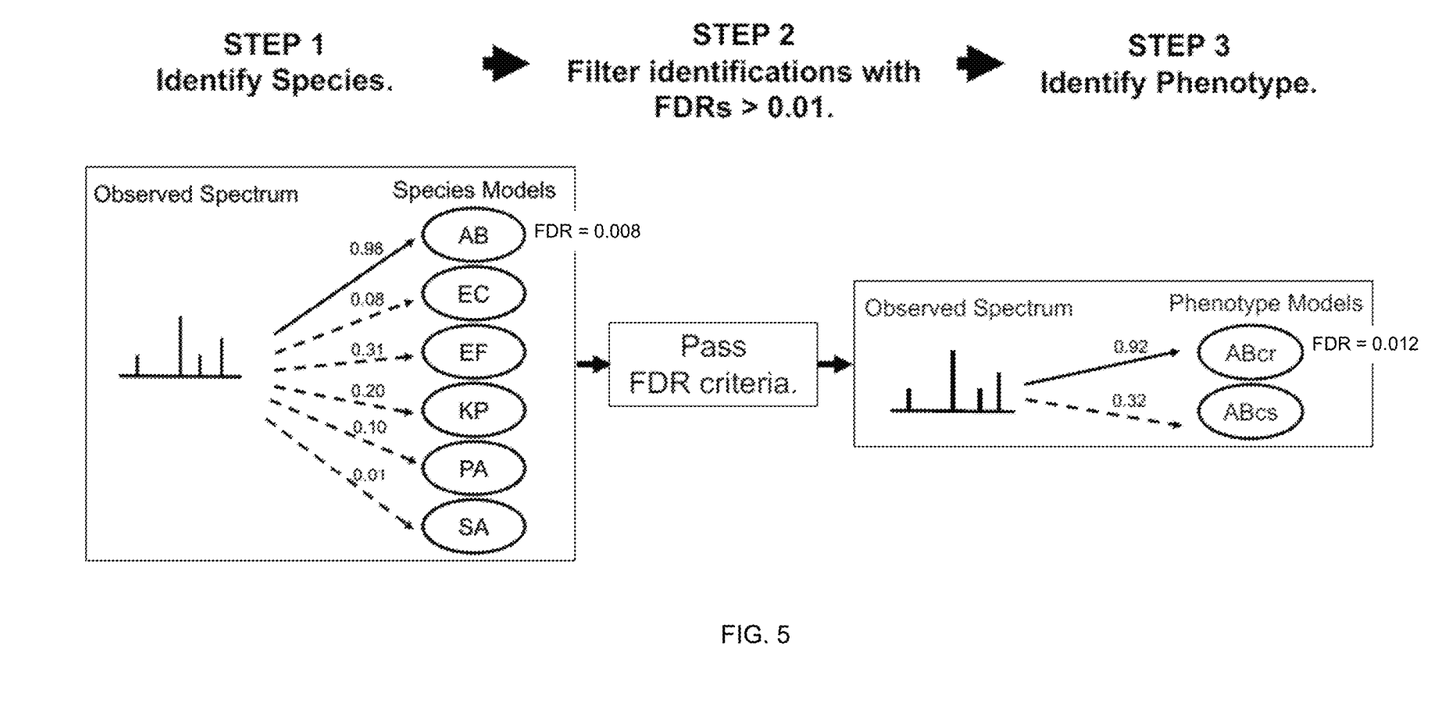
FIG. 5 depicts a general workflow of the Lipid A Spectral Library (LASL) technique according to an embodiment of the invention.

The general framework of Bacteria/Phenotype Identification is displayed in FIG. 5. Given a glycolipid mass spectrum, Applicant first identified bacteria. If the bacteria was identified with a high confidence (e.g., FDR<0.01) and its phenotype models were available in the Spectral Library, Applicant identified its phenotype. In detail, in Step 1, Applicant measured a predicted probability, $p_b$, that a given mass spectrum was from a microbial species b, where b represented species in spectral library. In this setting, $\Sigma_{b \in sL} p_b$ was not equal to 1 where SL was a set of all the species in spectral library because Applicant chose not to use m-group classification models where m>2.

Noting that in practice, a given mass spectrum may not be from microbial species in the spectral library, Applicant intentionally added decoy mass spectra in the training set and used $p_b$ as mere scores to choose the best species models. Applicant refers to $p_b$ as matching scores herein. After a matching score of the given mass spectrum for each species model was estimated, the species with the highest matching score was assigned to the mass spectrum as bacteria identification. Applicant denoted the top matching score as $p_b^*$.

In Step 2, Applicant measured uncertainty of bacteria identifications. Applicant notes that the spectral library may not contain a microbial species of interest. Even when the library contains such a species, misidentifications can occur. Because it will be important to be certain about bacterial identification of infected patients, Applicant calculated p-values and the corresponding false discovery rates (FDR) for the bacterial identifications and discarded identifications with their FDRs>0.01. The p-values were estimated using 10,000 decoy mass spectra in the test set:

$$p\text{-value} = \frac{\sum_{i=1}^{N_d} I(p_{d_i} > p_b *)}{N_d} \quad (1)$$

where d represents decoy mass spectrum, $N_d$ is the number of decoy mass spectra, I is the indicator variable, $p_{d_i}$ is the top matching score of ith decoy mass spectrum, $p_b^*$ is the top matching score of an observed (non-decoy) mass spectrum. In other words, the p-value was calculated by dividing the number of decoy mass spectra with their top matching score greater than the top matching score of a given non-decoy spectrum by the total number of decoy mass spectra. The false discovery rates were estimated to correct multiple testing errors as described in Benjamini 1995.

For the glycolipid mass spectra identified as either AB or KP with high confidence (FDRs<0.01), Applicant identified their phenotypes in Step 3 (FIG. 5). Note that once phenotypes for other species become available, similar procedures can be incorporated. Similar to species identifications, the given mass spectrum was matched to the available phenotype identification models and their matching scores were calculated. A phenotype with the top matching score was assigned to a given mass spectrum. The corresponding p-value and FDR were estimated.

LASL was implemented in the R programming language. Users can run it in one command line:

./LASL.Rscript

Currently, LASL contains the following six species: *Acinetobacter Baumannii, Enterobacter Cloacae, Enterococcus Faecalis, Klebsiella Pneumoniae, Pseudomonas Aeruginosa,* and *Staphylococcus Aureus*. Users can update the existing bacterial species models or add new models as they become available.

Existing Proteomics-Based Approaches

Applicant compared its approach to recently published bacterial identification approaches for whole cell typing described in Yang 2017. Yang 2017 proposed confidence scores based on spectra similarity scores and a bootstrap approach. Specifically, one similarity score they proposed was a relative Euclidean distance (ieu) weighted by peaks between spectrum a and b. Another score was cosine correlation (cosine).

Results and Discussion

LASL performed better than ieu and cosine in several aspects. LASL was able to correctly identify more (non-decoy) mass spectra than the proteomics-based approaches proposed by Yang 2017. The proportion of correctly assigned bacteria for LASL was 99.08%, compared to 90.49% and 84.27% for cosine and ieu, respectively. Euclidean distance was able to identify about 34% correctly and, thus, was not considered for the further comparison.

Figure 6A:
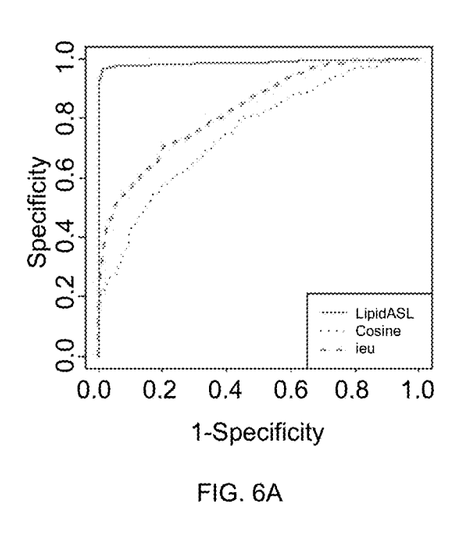
FIGS. 6A-6C provides a performance comparison in species identifications among LASL, cosine correlation (cosine), and intensity-weighted Euclidean distance (ieu) using Receiver Operating Characteristic (ROC) curves, Precision-Recall (PR) curves, and FDR Threshold vs. no. of identified species plot. The horizontal dotted line in FIG. 6C is the number of non-decoy mass spectra in test set.
Figure 6B:
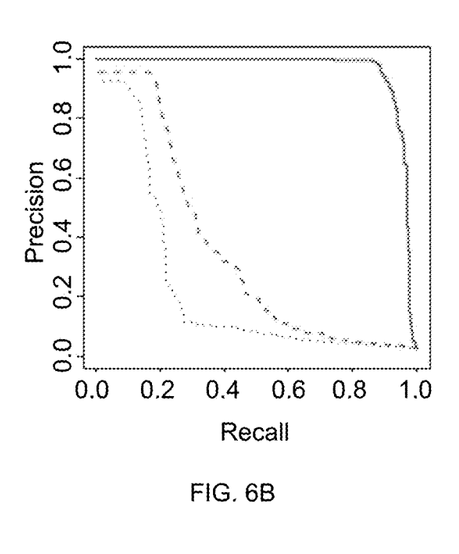

In addition, the proposed scores ($p_b^*$) were better at differentiating correct identifications from incorrect identifications (Table 2 and FIGS. 6A and 6B). Applicant used decoy mass spectra in test set to measure the discriminative power of the proposed scores. The matching scores ($p_b^*$) in LASL were good at differentiating correct from incorrect identifications with ROC AUC 98.84% and Recall-precision AUC 96.01%. In contrast, cosine and relative Euclidean distance (ieu) performed very poorly. The areas under ROC and Recall-Precision curves for cosine were 75.44% and 23.01%, respectively. For relative Euclidean Distance (ieu), they were 83.07% and 35.51%, respectively.

Most importantly, LASL identified 4.8 and 5.9 times more bacteria than ieu and cosine at false discovery rates <0.01 (Table 2).

TABLE 2

The performance comparison in bacterial identifications among LASL, intensity-weighted Euclidean similarity (ieu), and Cosine correlation (cosine). The number of identified species with FDR < 0.01, and area under curve (AUC) for receiver operating characteristic (ROC) curves and precision-recall (PR) curves were used to compare the performance.

| Methods | ROC AUC | PR AUC | # of IDs |
|---|---|---|---|
| LASL | 98.84% | 96.01% | 289 (305)* |
| Cosine | 75.44% | 23.01% | 42 (305)* |
| Ieu | 83.07% | 35.51% | 50 (305)* |

*The numbers in parentheses represent the total numbers of (non-decoy) mass spectra in test set.

Figure 6C:
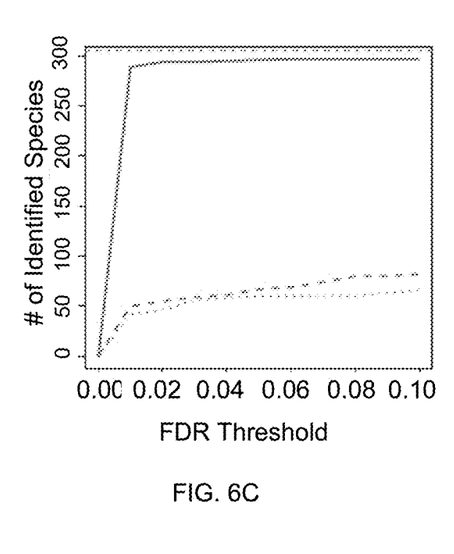

The other two approaches identified 50 or less mass spectra at FDRs<1%. Most LASL identifications had very low false discovery rates (FIG. 6C). Out of 305 non-decoy glycolipid mass spectra, LASL identified 289 non-decoy mass spectra at their FDRs<1%. Because true identifications in the test set were known, Applicant investigated how many mass spectra with their false discovery rates <0.01 were true identifications. Only one mass spectrum identified by LASL was a false identification at FDR<1%. The superior performance of LASL was expected since LASL was designed to analyze glycolipid mass spectra, while the other two approaches were designed to analyzed mass spectra generated from whole proteomic analysis. However, this comparison demonstrated the need for a bacterial identification bioinformatics tool based on glycolipid mass spectra.

LASL also performed well in identifying phenotypes when phenotypes of species were available in a spectral library (Table 3). At FDR <1%, LASL identified phenotypes of 130 AR spectral entries, which were 97% of AR mass spectra in the test set. At the same threshold, 66 out of 67 KP mass spectra had their phenotype identifications at FDR <1%. The area under curve calculations for ROC and Recall-Precision were over 94% for both AR and KP phenotype identifications. Applicant did not consider comparing our approach to ieu and cosine in phenotype identifications because the number of confidently identified bacteria for ieu and cosine were substantially smaller than LASL in bacterial identification stage.

TABLE 3

The performance of LASL in bacterial identifications. The number of identified species with FDR < 0.01, area under curve (AUC) for receiver operating characteristic (ROC) curves and precision-recall (PR) curves were used to measure the performance.

| Phenotypes | ROC AUC | PR AUC | # of IDs |
|---|---|---|---|
| ABcr vs. ABcs | 99.90% | 96.98% | 130 (134)* |
| KPcr VS. KPcs | 99.94% | 94.72% | 66 (67)* |

*The numbers in parentheses represent the total numbers of mass spectra identified as either AB or KP at FDR < 1% in test set.

LASL performed substantially better than proteomics-based bioinformatics approaches in terms of accurately identifying and characterizing bacteria. However, LASL can identify only bacteria that are present in the spectral library. Noting that the mass spectrometry technology needed for this assay is relatively low-cost, widely distributed in hospital clinics and easy to use, Applicant anticipates that the diversity of bacteria in this library will increases rapidly in the future.

Another way to overcome this is to utilize false-discovery rates. In practice, one may not know whether a bacterium of interest is present in a given spectral library, even when the library contains a wide variety of microbes. If a glycolipid mass spectrum of interest is not from bacteria in the spectral library, a best outcome would be that LASL assigns low matching scores ($p_b^*$) and high false discovery rates to such spectra. Thus, the identification of those mass spectra would be discarded, not passing the FDR threshold (e.g., 1%, 5%). When Applicant tested LASL with the supplementary dataset, which contained no species from the spectral library, the matching scores for those identifications were very small ranging from 0.01 to 0.02. Their false discovery rates were larger than 5%. High false-discovery rates or low matching scores of mass spectra do not necessarily imply that those spectra are not from bacteria in Applicant's spectral library because glycolipid mass spectra of bacteria from the spectral library can have low matching scores due to poor quality of mass spectra (e.g., low signal-to-noise). However, this demonstrated the potential use of Applicant's approach in practice in cases where the spectral library does not contain all bacteria.

CONCLUSION

Applicant developed a model-based spectral library framework to analyze MALDI-TOF-MS data of bacterial membrane glycolipids like Lipid A from Gram-negative bacteria and related species from Gram-positive bacteria. The performance of LASL was demonstrated using pathogens that were notorious for their hospital-acquired infections (HAIs) prevalence and acquisition of resistance to antibiotics. With the proposed framework, the library can be extended easily containing many pathogens. As the pathogen information in the library increases, Applicant believes that LASL can provide the valuable information to treat infected patients and save lives.

EQUIVALENTS

Although preferred embodiments of the invention have been described using specific terms, such description is for illustrative purposes only, and it is to be understood that changes and variations may be made without departing from the spirit or scope of the following claims.

INCORPORATION BY REFERENCE

The entire contents of all patents, published patent applications, and other references cited herein are hereby expressly incorporated herein in their entireties by reference.

REFERENCES

Benjamini, Y. and Hochberg, Y. (1995). Controlling the false discovery rate: A practical and powerful approach to multiple testing. Journal of the Royal Statistical Society. Series B (Methodological), 57(1), 289-300.

Chen, T. and Guestrin, C. (2016). XGBoost: A scalable tree boosting system. In Proceedings of the 22Nd ACM SIGKDD International Conference on Knowledge Discovery and Data Mining, KDD'16, pages 785-794. ACM.

Gibb, S. and Strimmer, K. (2012). MALDIquant: a versatile r package for the analysis of mass spectrometry data. Bioinformatics, 28(17), 2270-2271.

Leung, L. M., Fondrie, W. E., Doi, Y., Johnson, J. K., Strickland, D. K., Ernst, R. K., and Goodlett, D. R. (2017). Identification of the ESKAPE pathogens by mass spectrometric analysis of microbial membrane glycolipids. Scientific Reports, 7(1), 6403.

Ryan, C. G., Clayton, E., Griffin, W. L., Sie, S. H., and Cousens, D. R. (1988). SNIP, a statistics-sensitive background treatment for the quantitative analysis of PIXE spectra in geoscience applications. Nuclear Instruments and Methods in Physics Research Section B: Beam Interactions with Materials and Atoms, 34(3), 396-402.

Savitzky, A. and Golay, M. J. E. (1964). Smoothing and differentiation of data by simplified least squares procedures. Analytical Chemistry, 36(8), 1627-1639.

Yang, Y., Lin, Y., Chen, Z., Gong, T., Yang, P., Girault, H., Liu, B., and Qiao, L. (2017). Bacterial whole cell typing by mass spectra pattern matching with bootstrapping assessment. Analytical Chemistry, 89(22), 12556-12561.

The invention claimed is:

1. A computer-implemented method of identifying a species and phenotype from mass spectra, the computer-implemented method comprising:
   (a) loading a data set into memory on a computer, the data set comprising mass spectra;
   (b) pre-processing the mass spectra to identify at least ranks of intensities across bins defining ranges of mass-to-charge ratio;
   (c) applying species binary classifiers against at least the ranks of intensities;
   (d) identifying one or more species based on step (c);
   (e) calculating a False-Discovery Rate (FDR) for the one or more species using decoy members;
   (f) if the FDR is less than a pre-defined threshold, applying phenotype binary classifiers against at least the ranks of intensities; and
   (g) identifying one or more phenotypes based on step (f);
   wherein the species binary classifiers and the phenotype binary classifiers are trained using a machine-learning method, the machine-learning method comprising:
      loading a data set into memory on a computer, the data set comprising:
         a species and associated mass spectra; and
         a phenotype for each member of the data set;
      for each of the associated mass spectra, pre-processing to identify ranks of intensities of an in-bin peak across bins defining ranges of mass-to-charge ratio;
      training a species binary classifier for each of a plurality of species using at least the ranks of intensities; and
      training a phenotype binary classifier for each of a plurality of phenotypes.

2. The computer-implemented method of claim 1, wherein the machine learning method further comprises: introducing decoy members into the data set.

3. The computer-implemented method of claim 2, wherein the decoy members include shuffled ranks of intensities.

4. The computer-implemented method of claim 1, wherein the mass spectra were generated using negative ion MALDI-TOF-MS (Matrix-Assisted Laser Desorption/Ionization—Time Of Flight—Mass Spectrometry) analysis.

5. The computer-implemented method of claim 1, wherein the intensities are relative intensities.

6. The computer-implemented method of claim 1, wherein the species are bacterial species.

7. The computer-implemented method of claim 1, wherein the species are selected from the group consisting of: mouse, primate, human, mammal, and animal.

8. The computer-implemented method of claim 1, wherein the mass spectra are glycolipid mass spectra.

9. The computer-implemented method of claim 1, wherein the mass spectra are selected from the group consisting of: protein/peptide mass spectra and metabolite mass spectra.

10. The computer-implemented method of claim 1, wherein the applying step identifies a plurality of species and phenotypes for the single mass spectrum.

11. A system for identifying a species from mass spectra, the system comprising:
   a processor; and
   computer-readable memory containing instructions to:
      implement an interface programmed to receive mass spectra;
      store the mass spectra in the computer-readable memory; and
      invoke execution of a computer-implemented method of identifying a species and phenotype from mass spectra on the processor, the computer-implemented method comprising:
         (a) loading the mass spectra;
         (b) pre-processing the mass spectra to identify at least ranks of intensities across bins defining ranges of mass-to-charge ratio; and
         (c) applying species binary classifiers against at least the ranks of intensities;
         (d) identifying one or more species based on step (c);
         (e) calculating a False-Discovery Rate (FDR) for the one or more species using decoy members;
         (f) if the FDR is less than a pre-defined threshold, applying phenotype binary classifiers against at least the ranks of intensities; and
         (g) identifying one or more phenotypes based on step (f);
         wherein the species binary classifiers and the phenotype binary classifiers are trained using a machine-learning method, the machine-learning method comprising:
            loading a data set into memory on a computer, the data set comprising:
               a species and associated mass spectra; and
               a phenotype for each member of the data set;
            for each of the associated mass spectra, pre-processing to identify ranks of intensities of an in-bin peak across bins defining ranges of mass-to-charge ratio;
            training a species binary classifier for each of a plurality of species using at least the ranks of intensities; and
            training a phenotype binary classifier for each of a plurality of phenotypes.

* * * * *